(12) United States Patent
Simon

(10) Patent No.: US 6,358,500 B1
(45) Date of Patent: Mar. 19, 2002

(54) STABLE W/O/W EMULSION AND ITS USE AS COSMETIC AND/OR DERMATOLOGICAL COMPOSITION

(75) Inventor: Pascal Simon, Vitry sur Seine (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/314,953

(22) Filed: May 20, 1999

(30) Foreign Application Priority Data

May 20, 1998 (FR) ............................................. 98 06412

(51) Int. Cl.$^7$ .................................................. A61K 7/00
(52) U.S. Cl. ................................ 424/70.12; 424/70.19; 424/70.31; 424/401; 514/844; 514/846; 514/847; 514/938; 514/944; 514/945
(58) Field of Search ............................. 424/401, 70.12, 424/70.19, 70.31; 514/844, 846, 847, 938, 944, 945

(56) References Cited

U.S. PATENT DOCUMENTS

| | | | | |
|---|---|---|---|---|
| 5,407,677 A | * | 4/1995 | Tominaga et al. | |
| 5,412,004 A | * | 5/1995 | Tachibana et al. | |
| 5,747,009 A | * | 5/1998 | Hansenne | |
| 5,811,487 A | * | 9/1998 | Schulz, Jr. et al. | |
| 5,948,855 A | * | 9/1999 | Lin et al. | ............... 524/837 |

FOREIGN PATENT DOCUMENTS

| | | |
|---|---|---|
| EP | 0 631 774 | 1/1995 |
| EP | 0 780 114 | 6/1997 |
| FR | 2 693 466 | 1/1994 |

* cited by examiner

Primary Examiner—Diana Dudash
Assistant Examiner—Alysia Berman
(74) Attorney, Agent, or Firm—Oblon, Spivak, McClelland, Maier & Neustadt, P.C.

(57) ABSTRACT

A water/oil/water triple emulsion comprising an aqueous external phase and a W/O primary emulsion comprising an oily phase and an aqueous internal phase, which comprises at least one partially or completely crosslinked organopolysiloxane elastomer comprising a polyoxyethylenated and/or polyoxypropylenated chain. The emulsion may be used, for example for cleansing and/or treating and/or protecting the skin and/or mucous membranes and/or keratinous fibers.

23 Claims, No Drawings

STABLE W/O/W EMULSION AND ITS USE AS COSMETIC AND/OR DERMATOLOGICAL COMPOSITION

BACKGROUND OF THE INVENTION

1. Field of the Invention

The present invention relates to a stable water/oil/water triple emulsion and to its use, for example, in the cosmetics and/or dermatological fields, especially for the controlled release of active agents. The emulsion may be used, for example, for cleansing and/or treating and/or protecting the skin and/or mucous membranes and/or keratinous fibers.

2. Background of the Invention

The use is known, in particular in the cosmetics and dermatological fields, of topical compositions in the form of emulsions. These emulsions are generally oil-in-water (O/W) or water-in-oil (W/O) emulsions. These compositions may also be multiple emulsions of the water/oil/water (W/O/W) or oil/water/oil (O/W/O) type. Use is preferably made, among multiple emulsions, of emulsions with an aqueous external phase, namely W/O/W emulsions, which combine the advantages of freshness on application, contributed by the water present in the aqueous external phase, and of comfort, contributed by a relatively large amount of oil.

However, multiple emulsions are not exploited to any great extent because they frequently exhibit problems of stability over time. The most frequently encountered mechanism for destabilization is the migration of water from the internal droplets to the aqueous external environment through the intermediate oily layer, either by simple diffusion of water through the oily membrane or by prior rupture of the oily film, bringing about the coalescence of the internal droplets of water and resulting in a release of internal water into the aqueous external environment. Generally, this phenomenon, known as loss of the multiple nature, ends up by bringing about macroscopically visible phase separation and the production of a simple O/W emulsion in place of a triple emulsion.

Various means have consequently been envisaged to mitigate this disadvantage. In particular, one of the solutions is adding, into the aqueous internal phase or into the aqueous external phase, one or more gelling polymer(s), the role of which is to limit, on a long-term basis, the movements of water from the internal phase to the external phase. However, the multiple emulsions obtained exhibit the drawback of being sticky and of taking a long time to penetrate into the skin, because of the presence of large amounts of polymers which, because of their polymeric structure, remain at the surface of the skin.

Another solution is introducing lipophilic structuring agents into the oily phase. Thus, FR-A-2,679,788 describes the use of unsaturated linear $C_8$ to $C_{14}$ fatty alcohols, which give rise to soaps and which confer a gel structure on the emulsion. Unfortunately, the sensorial qualities of the emulsions obtained are not very satisfactory because they have a tendency to become waxy on application to the skin. In addition, the presence of soaps in the emulsion has the consequence of causing soaping, i.e., whitening during application to the skin.

In addition, the use is known, for example as described by WO-A-94/1073, in triple emulsions of silicone polymers comprising a polyoxyethylenated and/or polyoxypropylenated chain, which, although polymers, do not have the above mentioned disadvantages. However, the use of this type of emulsifier requires the presence of a certain amount of silicone oil in the oily phase and therefore limits the pharmaceutical dosage composition of the triple emulsion. In addition, in order to obtain satisfactory stability of the triple emulsion, it is often necessary to add a gelling agent to one of the aqueous phases.

The need therefore remains for a stable W/O/W multiple emulsion which does not have the disadvantages of known emulsions and which is, in particular, pleasant to use on the skin while contributing, for example, the advantages of an emulsion with an aqueous external phase.

SUMMARY OF THE INVENTION

The inventors have now found, unexpectedly, that the introduction of a partially or completely crosslinked organopolysiloxane elastomer comprising a polyoxyethylenated and/or polyoxypropylenated chain into a water/oil/water (W/O/W) triple emulsion makes it possible to stabilize the emulsion without requiring the addition of other stabilizing agents.

Accordingly, the present invention provides a water/oil/water triple emulsion comprising an aqueous external phase and a W/O primary emulsion comprising an oily phase and an aqueous internal phase, characterized in that it comprises at least one partially or completely crosslinked organopolysiloxane elastomer comprising a polyoxyethylenated and/or polyoxypropylenated chain.

Another aspect of the present invention is the use of at least one partially or completely crosslinked organopolysiloxane elastomer comprising a polyoxyethylenated and/or polyoxypropylenated chain for the stabilization of a water/oil/water triple emulsion.

For topical application, the inventive emulsion may contain a topically acceptable medium, i.e., a medium compatible with the skin, mucous membranes and/or keratinous fibers, such as the hair.

The triple emulsion according to the invention has the advantage of being stable and of being able in particular to retain the activity of active agents present in the aqueous internal phase, whence they are released during the application of the composition to the skin, mucous membranes and/or hair.

A more complete appreciation of the invention and many of the attendant advantages thereof will be readily obtained as the same becomes better understood by reference to the following detailed description.

DETAILED DESCRIPTION OF THE INVENTION

The partially or completely crosslinked organopolysiloxane elastomers which may be used in the inventive emulsion are preferably introduced into the oily phase of the emulsion. They are generally emulsifiers. They can be chosen in particular from the crosslinked polymers disclosed in EP-A-0,545,002. U.S. Pat. No. 5,412,004, which is equivalent to EP-A-0,545,002 is incorporated herein by reference. These organopolysiloxanes are obtained by addition polymerization of the following compounds (I) and (II):

(I) an organohydropolysiloxane of formula (1):

$$R^1{}_a R^2{}_b H_c SiO_{(4-a-b-c)/2} \tag{1}$$

in which $R^1$ represents a substituted or unsubstituted alkyl, aryl or aralkyl group comprising from 1 to 18 carbon atoms or a halogenated hydrocarbon-comprising group; $R^2$ represents a group:

  (3)

in which $R^3$ is a hydrogen, a saturated aliphatic hydrocarbon-comprising group having from 1 to 10 carbon atoms or a —(CO)—$R^5$ group where $R^5$ is a saturated aliphatic hydrocarbon-comprising group having from 1 to 5 carbon atom; d is an integer from 0 to 200, provided that d+e is a number ranging from 3 to 200, and n is a number from 2 to 6, a is a value satisfying the inequality: $1.0 \leq a \leq 2.5$, b is a value satisfying the inequality: $0.001 \leq b \leq 1.0$ and c is a value satisfying the inequality: $0.001 \leq c \leq 1.0$;

or an organohydropolysiloxane represented by the following formula (2):

$$R^1_f H_g SiO_{(4-f-g)/2} \quad (2)$$

in which $R^1$ has the same meaning as in the formula (1), f is a value satisfying the inequality: $1.0 \leq f \leq 3.0$ and g is a value satisfying the inequality: $0.001 \leq g \leq 1.5$;

or a mixture of the organohydropolysiloxanes of formulae (1) and (2), and (II) a polyoxyalkylene represented by the following formula (A):

$$C_m H_{2m} O(C_2 H_4 O)_h (C_3 H_6 O)_i C_m H_{2m-1} \quad (A)$$

in which h is an integer ranging from 2 to 200, i is an integer ranging from 0 to 200, provided that h+i is a number ranging from 3 to 200, and m is a number ranging from 2 to 6, or an organopolysiloxane represented by the following formula (B):

$$R^1_j R^4_k SiO_{(4-j-k)/2} \quad (B)$$

in which $R^1$ has the same meaning as in the formula (1), $R^4$ is a monovalent hydrocarbon-comprising group having an unsaturated aliphatic bond at the end and comprising 2 to 10 carbon atoms, j is a value satisfying the inequality: $1.0 \leq j \leq 3.0$ and k is a value satisfying the inequality: $0.001 \leq k \leq 1.5$, or a mixture of the polyoxyalkylene of formula (A) and of the organopolysiloxane of formula (B), where at least one organohydropolysiloxane of formula (1) or at least one polyoxyalkylene of formula (A) is present as essential component of the addition polymerization.

The organopolysiloxane is preferably mixed with a silicone oil and/or a polyol and is prepared directly as such a mixture. The silicone oil preferably exhibits a viscosity equal to or less than 100 cSt at 25° C. According to one embodiment of the invention, the organopolysiloxane elastomer is prepared from 100 parts by weight of the constituents defined above and 3 to 200 parts by weight of a silicone oil having a viscosity equal to or less than 100 cSt at 25° C. and/or of a polyol. The silicone oil can be a volatile or non-volatile silicone oil or a mixture of volatile silicone oil and of non-volatile silicone oil.

The organopolysiloxanes of the invention are in particular obtained according to the procedure of Examples 3, 4 and 8 of EP-A-545,002 (or U.S. Pat. No. 5,412,004, incorporated herein by reference) and of the Examples of U.S. Pat. No. 5,811,487 (incorporated herein by reference).

The organopolysiloxanes of the composition of the invention comprise one or more oxyalkylenated and in particular oxyethylenated (OE) groups, for example from 1 to 40 oxyalkylenated units and better still 1 to 20 oxyalkylenated units, which can form polyoxyalkylene and in particular polyoxyethylene chains. These groups can be pendant, at the chain end or intended to connect two parts of the silicone structure. The silicon atoms carrying these groups number from approximately 1 to 10.

Although the invention relates more preferably to organopolysiloxanes comprising (an) oxyethylenated group(s), the organopolysiloxanes may also contain (an) oxypropylenated group(s). The organopolysiloxanes can also simultaneously comprise one or more oxyethylenated (OE) group(s), for example 1 to 20, and one or more oxypropylenated (OP) group(s), for example 0 to 20; these organopolysiloxanes are also known as organopolysiloxanes comprising (an) alkylethoxy-propylenated group(s). The number of oxyethylenated groups is preferably greater than the number of oxypropylenated groups.

A partially or completely crosslinked organopolysiloxane comprising a polyoxyethylenated and/or polyoxypropylenated chain, the product sold by Shin-Etsu under the name of KSG21 may be used. This product comprises 38% of organopolysiloxane and 62% of silicone oil having a viscosity of 6 cSt. Mention may be made also of the product of the example 3 of U.S. Pat. No. 5,412,004, which comprises about 33% of organopolysiloxane and 67% of silicone oil having a viscosity of 6 cSt.

In the triple emulsion of the present invention, the partially or completely crosslinked organopolysiloxane is preferably used in an amount of active material ranging from 0.1 to 10% and preferably from 1 to 5% of the total weight of the triple emulsion. These ranges include all specific values and subranges therebetween, including 0.2, 0.5, 1.5, 2, 3, 4, 6 and 8% by weight.

The aqueous external phase of the triple emulsion preferably comprises at least one nonionic surfactant having an HLB (Hydrophilic Lipophilic Balance) of greater than 12 and the primary emulsion comprises at least one nonionic surfactant having an HLB of less than 8.

The nonionic surfactant of HLB>12 optionally present in the triple emulsion may be, for example, an ethoxylated or ethoxylated/propoxylated fatty alcohols with a fatty chain comprising from 12 to 22 carbon atoms, ethoxylated sterols, such as PEG-16 soya sterol or PEG-10 soya sterol, polyoxyethylene polyoxypropylene block polymers (poloxamers) and their mixtures. Ethoxylated sterols and of poloxamers are preferred.

The amount of surfactant in the aqueous external phase can range, for example, from 0.5 to 5% and preferably from 1 to 3% of the total weight of the triple emulsion. These weight ranges include all specific valves and subranges therebetween, including 0.75, 1.5, 2 and 2.5% by weight.

The nonionic surfactant of HLB<8 can be chosen in particular from glyceryl esters, such as mono-, di- or triglyceryl mono-, di- or triisostearate or -oleate, sugar esters, such as sucrose or methyl glucose mono- or diisostearate or -oleate, alkylpolyglucoside ethers, such as oleyl- or isostearylpolyglucoside, and their mixtures. Sugar esters and alkylpolyglucoside ethers are preferred.

The amount of surfactant in the primary emulsion according to the invention can range, for example, from 0.01 to 5% and preferably from 0.5 to 3% of the total weight of the triple emulsion. These ranges include all specific values and subranges therebetween, including 0.02, 0.05, 0.1, 0.2, 1, 2 and 4% by weight.

The oily phase of the primary emulsion comprises one or more fatty substances chosen from oils of animal origin, oils of vegetable origin (apricot kernel oil), mineral oils (liquid petrolatum), synthetic oils (isohexadecane), fluorinated oils, waxes, in particular silicone waxes, silicone gums or silicone resins.

The amount of fatty substances preferably ranges from 2 to 40% and better still from 5 to 30% of the total weight of the triple emulsion. These ranges include all specific values and subranges therebetween, including 3, 8, 10, 15, 20, 25 and 30% by weight.

The primary emulsion can represent, for example, from 5 to 70% and preferably from 10 to 65% of the total weight of the triple emulsion. These ranges include all specific values and subranges therebetween, including 8, 15, 20, 25, 30, 40, 50 and 60% by weight.

The triple emulsion is prepared conventionally by preparation of the primary emulsion and incorporation of a predetermined amount of the primary emulsion in the aqueous external phase.

As discussed above, one of the major advantages of the emulsion in accordance with the invention is that the latter can comprise both cosmetic and therapeutic active agents while exhibiting a stable nature, it therefore being possible for these active agents to be chosen in particular from all those commonly used to date in the field of cosmetics, dermatology or medicine.

Another subject-matter of the invention is therefore a topical composition, characterized in that it comprises an emulsion as defined above and at least one active agent.

Non-limiting examples of active agents include polyols, such as glycerol, glycols and sugar derivatives, beta-hydroxy acids, such as salicylic acid and derivatives thereof, alpha-hydroxy acids, such as lactic acid and glycolic acid, screening agents, moisturizers, such as protein hydrolysates, vitamins such as vitamin E, and mixtures thereof.

In addition, the inventive composition makes it possible to stabilize any active agent which is unstable in oxidizing medium and mention may in particular be made, as active principles which are unstable in oxidizing medium, of vitamins and in particular ascorbic acid (vitamin C) and derivatives thereof, in particular its glycosyl and phosphate derivatives, and its esters, such as ascorbyl acetate, palmitate and propionate, or retinol (vitamin A) and derivatives thereof, in particular its esters, such as retinyl acetate, palmitate and propionate;

urea; rutin; enzymes, such as lipase, protease, phospholipase and cellulases; natural extracts, such as green tea, balm extract, thyme extract or procyanidol oligomers (PCO), such as hawthorn PCO, pine PCO and grapeseed PCO; certain acids, such as kojic acid, caffeic acid, retinoic acid and derivatives thereof, or benzene-1,4-di(3-methylidene-10-camphorsulphonic acid); carotenoids, such as carotenes, such as, for example, α-, β- and γ-carotenes, β,Φ-carotene, ξ-carotene, β,λ-carotene or lycopene (Ψ,Ψ-carotene); or polyunsaturated fatty acids, such as gamma-linolenic acid, and mixtures thereof.

It can also relate to any natural or synthetic compound which may comprise the active agents indicated above, in particular plant extracts and more especially fruit extracts.

The composition of the invention is particularly advantageous in stabilizing vitamins, in particular vitamin C and vitamin A, and carotenoids, in particular lycopene.

The amount of active agents in the composition according to the invention depends on the type of active agents used and on the desired purpose. Generally, the active agent or agents can be used in the composition according to the invention in an amount ranging from 0.01 to 20% by weight, preferably from 0.04 to 15% and better still from 0.1 to 10% by weight with respect to the total weight of the composition. These ranges include all specific values and subranges therebetween such as 0.02, 0.05, 0.2, 0.5, 1, 2, 5 and 15% by weight.

According to the hydrophilic or lipophilic nature of the active agents used, the latter are introduced into the oily phase of the composition or into one of the aqueous phases, preferably the aqueous internal phase.

The W/O/W emulsions can be used in various topical applications, in particular cosmetic and/or dermatological applications. The composition based on this emulsion can constitute in particular compositions for cleansing, protecting, treating and/or caring for the skin, mucous membranes and/or hair, in particular for the face, for the neck, for the hands, for the hair, for the scalp or for the body, as well as for the eyelashes. An effective amount of the emulsion or a composition containing the emulsion may be applied to skin, mucous membranes and/or hair desired to be treated.

The inventive emulsion may be a further subject-matter of the invention is consequently the cosmetic use of the composition according to the invention for cleansing and/or treating and/or protecting the skin and/or mucous membranes and/or keratinous fibers, that is to say the hair and/or eyelashes.

Included in the present invention is the use of the composition according to the invention for the preparation of a composition intended to cleanse and/or treat and/or protect the skin and/or mucous membranes and/or keratinous fibers, that is to say the hair and/or eyelashes.

Another facet of the present invention is a process for cleansing and/or treating and/or protecting the skin, mucous membranes and/or keratinous fibers, characterized in that it consists in applying a composition as defined above to the skin, mucous membranes and/or keratinous fibers.

The composition according to the invention may also begin the form of, for example, protective, treatment or care creams for the face, for the hands or for the feet, protective or care body milks, or lotions, gels or foams for caring for the skin, mucous membranes, hair and scalp.

The composition of the invention may also comprise lipophilic or hydrophilic adjuvants which are standard in the cosmetics or dermatological fields, such as surfactants, in particular foaming surfactants, preservatives, antioxidants, sequestering agents, solvents, fragrances, fillers, screening agents, odor absorbers, coloring materials and lipid vesicles. The amounts of these various items are those conventionally used in the fields under consideration, for example from 0.01 to 15% of the total weight of the composition, inclusive of all specific values and subranges therebetween such as 0.02, 0.05, 1, 2, 5, 8, 10 and 15% by weight. It can also comprise lipid vesicles formed from ionic or nonionic lipids.

These adjuvants, depending on their nature, can be introduced into the oily phase or into one of the aqueous phases.

EXAMPLES

Having generally described this invention, a further understanding can be obtained by reference to certain specific examples which are provided herein for purposes of illustration only and are not intended to be limiting unless otherwise specified. The amounts listed are % by weight.

Example 1

Emulsion

1. Primary emulsion:

Phase A:

| | |
|---|---|
| Methyl glucose dioleate | 1.5% |
| Liquid paraffin | 3.8% |
| Apricot kernel oil | 4.2% |
| Isohexadecane | 3.6% |
| Cyclohexamethylsiloxane | 4.5% |
| KSG 21 (comprising 28% of A.M.) | 2.4% |

Phase B:

| | |
|---|---|
| Magnesium sulphate | 0.4% |
| Glycerol | 3% |
| Water | 39.2% |

2. Triple emulsion:

Phase A:

| | |
|---|---|
| Primary emulsion | 62.6% |

Phase B:

| | |
|---|---|
| Cetyl alcohol | 0.7% |
| PEG-10 soya sterol | 2% |
| Preservative | 0.5% |
| Fragrance | 0.3% |
| Demineralized water | q.s. for 100% |

A composition identical to that of Example 1 was prepared by replacing the KSG 21 with a dimethicone copolyol (at 10% in cyclomethicone).

The emulsion obtained is a simple emulsion and not a triple emulsion.

This shows that only the combination according to the invention makes it possible to obtain the stable triple emulsion.

Example 2

Emulsion

1. Primary emulsion:

Phase A:

| | |
|---|---|
| Methyl glucose dioleate | 1.5% |
| Liquid paraffin | 3.8% |
| Apricot kernel oil | 4.2% |
| Isohexadecane | 3.6% |
| Cyclohexamethylsiloxane | 4.5% |
| KSG 21 (comprising 28% of A.M.) | 2.4% |

Phase B:

| | |
|---|---|
| Magnesium sulphate | 0.4% |
| Glycerol | 10% |
| Vitamin C | 3% |
| Water | 29.2% |

2. Triple emulsion:

Phase A:

| | |
|---|---|
| Primary emulsion | 62.6% |

Phase B:

| | |
|---|---|
| Cetyl alcohol | 0.7% |
| PEG-10 soya sterol | 2% |
| Preservative | 0.5% |
| Fragrance | 0.3% |
| Demineralized water | q.s. for 100% |

Example 3: Emulsion

1. Primary emulsion:

Phase A:

| | |
|---|---|
| Silicon oil cSt | 12% |
| Organopolysiloxane of the example 3 of the document U.S. Pat. 5,412,004) (about 6% of A.M.) | 18% |

Phase B:

| | |
|---|---|
| Magnesium sulphate | 0.7% |
| Water | qsp 100% |

2. Triple emulsion:

Phase A:

| | |
|---|---|
| Primary emulsion | 80% |

Phase B:

| | |
|---|---|
| Poloxamer 407 (Synperonic PE/F from the society ICI) | 0.8% |
| Preservative | 0.5% |
| Demineralized water | q.s. for 100% |

A stable triple emulsion is obtained.

Example 4: Emulsion

1. Primary emulsion:

Phase A:

| | |
|---|---|
| Silicon oil | 12% |
| Organopolysiloxane of the example 3 of the document U.S. Pat No. 5,412,004) (about 6% of A.M.) | 18% |

Phase B:

| | |
|---|---|
| Magnesium sulphate | 0.7% |
| Water | qsp 100% |

2. Triple emulsion:

Phase A:

| | |
|---|---|
| Primary emulsion | 80% |

Phase B:

| | |
|---|---|
| Cetyl alcohol | 0.7% |
| PEG-10 soya sterol | 2% |
| Preservative | 0.5% |
| Demineralized water | q.s. for 100% |

A stable triple emulsion is obtained.

Obviously, additional modifications and variations of the present invention are possible in light of the above teachings. It is therefore to be understood that within the scope of the appended claims, the invention may be practiced otherwise than as specifically described herein.

French Patent Application Ser. No. 98-06412, filed on May 20, 1998, is incorporated herein by reference.

What is claimed is:

1. A water/oil/water triple emulsion, comprising an aqueous external phase and a W/O primary emulsion, wherein the primary emulsion comprises an oily phase and an aqueous internal phase, wherein the triple emulsion comprises at least one partially or completely crosslinked organopolysiloxane elastomer comprising a polyoxyethylenated chain, or a polyoxypropylenated chain, or both a polyoxyethylenated chain and a polyoxypropylenated chain.

2. The emulsion of claim 1, wherein the organopolysiloxane elastomer is obtained by addition polymerization of compounds (I) and (II):

(I) an organohydropolysiloxane represented by formula (1):

$$R^1_a R^2_b H_c SiO_{(4-a-b-c)/2} \qquad (1)$$

wherein $R^1$ represents a substituted or unsubstituted alkyl, aryl or aralkyl group comprising from 1 to 18 carbon atoms or a halogenated hydrocarbon-comprising group; $R^2$ is a group represented by formula (3):

$$-C_n H_{2n} O(C_2 H_4 O)_d (C_3 H_6 O)_e R^3 \qquad (3)$$

wherein $R^3$ is a hydrogen, a saturated aliphatic hydrocarbon-comprising group having from 1 to 10 carbon atoms or a —(CO)—$R^5$ group wherein $R^5$ is a saturated aliphatic hydrocarbon-comprising group having from 1 to 5 carbon atoms; d is an integer from 2 to 200 and e is an integer from 0 to 200, provided that d+e is a number ranging from 3 to 200, and n is a number from 2 to 6, a is a value satisfying the inequality: $1.0 \leq a \leq 2.5$, b is a value satisfying the inequality: $0.001 \leq b \leq 1.0$ and c is a value satisfying the inequality: $0.001 \leq c \leq 1.0$;

or an organohydropolysiloxane represented by formula (2):

$$R^1_f H_g SiO_{(4-f-g)/2} \qquad (2)$$

wherein $R^1$ is as defined above for formula (1), f is a value satisfying the inequality: $1.0 \leq f \leq 3.0$ and g is a value satisfying the inequality: $0.001 \leq g \leq 1.5$;

or a mixture of the organohydropolysiloxanes represented by formula (1) and (2), and (II) a polyoxyalkylene represented by formula (A):

$$C_m H_{2m} O(C_2 H_4 O)_h (C_3 H_6 O)_i C_m H_{2m-1} \qquad (A)$$

wherein h is an integer ranging from 2 to 200, i is an integer ranging from 0 to 200, provided that h+i is a number ranging from 3 to 200, and m is a number ranging from 2 to 6, or an organopolysiloxane represented by formula (B):

$$R^1_j R^4_k SiO_{(4-j-k)/2} \qquad (B)$$

wherein $R^1$ is as defined above for formula (1), $R^4$ is a monovalent hydrocarbon-comprising group having an unsaturated aliphatic bond at the end and comprising 2 to 10 carbon atoms, j is a value satisfying the inequality: $1.0 \leq j \leq 3.0$ and k is a value satisfying the inequality: $0.001 \leq k \leq 1.5$, or a mixture of the polyoxyalkylene represented by formula (A) and the organopolysiloxane represented by formula (B), wherein at least one organohydropolysiloxane represented by formula (1) or at least one polyoxyalkylene represented by formula (A) is used in the addition polymerization.

3. The emulsion of claim 1, wherein the organopolysiloxane is mixed with a silicone oil or a polyol or both a silicone oil and polyol.

4. The emulsion of claim 3, wherein the silicone oil has a viscosity equal to or less than 100 cSt at 25° C.

5. The emulsion of claim 3, wherein the silicone oil has a viscosity equal to 6 cSt at 25° C.

6. The emulsion of claim 3, wherein the silicone oil is a volatile silicone oil or a nonvolatile silicone oil or a mixture thereof.

7. The emulsion of claim 1, wherein the triple emulsion comprises 0.1 to 10% by weight of the organopolysiloxane.

8. The emulsion of claim 1, wherein the aqueous external phase comprises at least one nonionic surfactant having an HLB of greater than 12.

9. The emulsion of claim 8, wherein the nonionic surfactant is selected from the group consisting of ethoxylated fatty alcohols with fatty chain comprising from 12 to 22 carbon atoms, ethoxylatedpropoxylated fatty alcohols with a fatty chain comprising from 12 to 22 carbon atoms, ethoxylated sterols, polyoxyethylene polyoxypropylene block polymers, and mixtures thereof.

10. The emulsion of claim 1, wherein the primary emulsion comprises a nonionic surfactant with an HLB<8.

11. The emulsion of claim 10, wherein the nonionic surfactant is selected from the group consisting of glyceryl esters, sugar esters, alkylpolyglucoside ethers, and mixtures thereof.

12. The emulsion of claim 1, wherein the oily phase comprises one or more fatty substances selected from the groups consisting of oils of animal origin, oils of vegetable origin, mineral oils, synthetic oils, fluorinated oils, waxes, silicone gums, and silicone resins.

13. The emulsion of claim 12, wherein the amount of fatty substances ranges from 2 to 40% of the total weight of the triple emulsion.

14. The emulsion of claim 1, wherein the primary emulsion represents from 5 to 70% of the total weight of the triple emulsion.

15. The emulsion of claim 1, wherein at least a portion of the organopolysiloxane is contained in the primary emulsion.

16. A composition suitable for topical application, comprising the emulsion of claim 1 and at least one active agent, wherein the active agent is a cosmetic or therapeutic active agent.

17. The composition of claim 16, wherein the active agent is selected from the group consisting of polyols, vitamins, beta-hydroxy acids, alpha-hydroxy acids, screening agents, moisturizers, active agents which are unstable in an oxidizing medium, and mixtures thereof.

18. The composition of claim 17, wherein the active agent is selected from the group consisting of vitamin C, vitamin A, urea, rutin, enzymes, natural extracts, procyanidol oligomers, carotenoids, polyunsaturated fatty acids, and mixtures thereof.

19. The composition of claim 16, wherein the active agent is present in a concentration ranging from 0.01 to 20% of the total weight of the composition.

20. The composition of claim 16, which comprises at least one lipophilic or hydrophilic adjuvant selected from the group consisting of preservatives, antioxidants, sequestering agents, solvents, fragrances, fillers, screening agents, odor absorbers, coloring materials, and lipid vesicles.

21. A method of W cleansing or treating or protecting the skin or (2) cleansing, treating or protecting mucous membranes or (3) cleansing, treating or protecting keratinous fibers, comprising applying an effective amount of the composition of claim 16 to the skin or mucous membranes or keratinous fibers, respectively.

22. A method of stabilizing a water/oil/water triple emulsion, comprising incorporating into the triple emulsion at least one partially or completely crosslinked organopolysiloxane elastomer comprising a polyoxyethylenated chain, or a polyoxypropylenated chain, or both a polyoxyethylenated chain and a polyoxypropylenated chain.

23. A method of making the triple emulsion of claim 1, comprising incorporating the organopolysiloxane into a water/oil/water triple emulsion.

* * * * *